United States Patent
Weekes

(10) Patent No.: US 8,398,642 B2
(45) Date of Patent: Mar. 19, 2013

(54) DUAL REAMER DRIVER

(75) Inventor: Stuart Weekes, Oxford (GB)

(73) Assignee: Symmetry Medical, Inc., Warsaw, IN (US)

( * ) Notice: Subject to any disclaimer, the term of this patent is extended or adjusted under 35 U.S.C. 154(b) by 471 days.

(21) Appl. No.: 12/233,149

(22) Filed: Sep. 18, 2008

(65) Prior Publication Data

US 2009/0082771 A1    Mar. 26, 2009

Related U.S. Application Data

(60) Provisional application No. 60/973,919, filed on Sep. 20, 2007.

(51) Int. Cl.
*A61B 17/00* (2006.01)

(52) U.S. Cl. ............... 606/80; 606/81; 606/91; 606/99; 606/86 A; 606/86 B

(58) Field of Classification Search ............... 606/80, 606/81, 91, 99, 86 A, 86 B, 914–916; 81/486, 81/491, 492, 487; 279/106, 107, 77, 78, 279/155

See application file for complete search history.

(56) References Cited

U.S. PATENT DOCUMENTS

| | | | |
|---|---|---|---|
| 3,702,611 A | 11/1972 | Fishbein | |
| 5,062,749 A * | 11/1991 | Sheets | 279/75 |
| 5,501,686 A * | 3/1996 | Salyer | 606/79 |
| 5,553,675 A | 9/1996 | Pitzen et al. | |
| 5,658,290 A | 8/1997 | Lechot | |
| 5,817,096 A | 10/1998 | Salyer | |
| 5,980,170 A * | 11/1999 | Salyer | 408/239 R |
| 6,126,359 A | 10/2000 | Dittrich et al. | |
| 6,258,107 B1 | 7/2001 | Balazs et al. | |
| 6,283,972 B1 | 9/2001 | Riley | |
| 6,854,742 B2 | 2/2005 | Salyer et al. | |
| 7,115,119 B2 * | 10/2006 | Desarzens | 606/1 |
| 7,229,078 B2 | 6/2007 | Lechot | |
| 7,326,198 B2 | 2/2008 | Desarzens et al. | |
| 2002/0111632 A1* | 8/2002 | Lechot | 606/86 |
| 2003/0216716 A1* | 11/2003 | Desarzens | 606/1 |
| 2004/0133210 A1 | 7/2004 | Wolford | |
| 2007/0123891 A1 | 5/2007 | Ries et al. | |
| 2007/0191854 A1* | 8/2007 | Grim | 606/80 |

* cited by examiner

*Primary Examiner* — Kevin T Truong
*Assistant Examiner* — Samuel Hanna
(74) *Attorney, Agent, or Firm* — Taylor IP, P.C.

(57) ABSTRACT

The disclosure illustrates a dual driver for surgical reamers in which either of a crossbridge and crossbar style reamers are axially inserted in the distal end of a central shaft for the reamer driver. A pair of L shaped grips are adapted to connect and disconnect the different style of reamers by the movement of an external sleeve biased towards the connection position. Movement of the sleeve away from the distal end allows an internal plunger to cam the grips to an open position and urge the appropriate reamer from the tool driver directly in an axial direction.

6 Claims, 5 Drawing Sheets

DUAL REAMER DRIVER

This is a non-provisional application based upon U.S. provisional patent application Ser. No. 60/973,919, entitled "AUTOMATIC DUAL CONNECTION REAMER DRIVE", filed Sep. 20, 2007, which is incorporated herein by reference.

BACKGROUND OF THE INVENTION

Field of the Invention

The present invention relates to orthopedic surgical reamers and more specifically to drivers for such tools.

In the field of orthopaedic surgery, it is often necessary to remove bone material to enable implantation of prosthesis to repair joints in the human body. Patella cutters and acetabular reamer cups and glenoid reamers are surgical tools which are used in surgery for the insertion of artificial joints. Acetabular reamer cups are used to cut hemispherical cavities in pelvis bones for the insertion of artificial hip joints. Patella cutters are used to shape the underside of the patella or knee cap during knee replacement surgery. Glenoid reamers are used to cut hemispherical cavities in shoulder bones for the insertion of artificial shoulder joints. Patella cutters have a complex arrangement of precisely shaped cutting edges arranged around an axis of rotation for cutting the patella. Acetabular reamer cups and glenoid reamers have a complex arrangement of cutting edges arranged on a spherical surface around the axis of rotation of the cup.

A number of tools have been developed for this purpose and include reamers having generally semi-hemispherical configuration with cutting elements on them so that a corresponding semi-hemispherical hollow can be formed in the bone material for providing a foundation for the repair of the joint.

There are two major driver styles in the field, one of which is for the Othy style manufactured by Symmetry Medical, Inc. and the other style manufactured by Precimed SA of L'Echelette, Switzerland. Although these both have semi-hemispherical cutting heads, they have different interfaces between driving tools with which they are associated. The Othy style has a crossbridge element. This element is a bar extending between the circumference of the hemisphere and having a circular expanded section in the middle. Numerous arrangements are available for securing this device as exemplified by U.S. Pat. No. 6,854,742. Alternatively, the Precimed reamer has a crossbar shape in which two circular cross section bars intersect at the center and extend to the walls of the hemisphere. An example of a driver for this type is found in U.S. Pat. No. 5,658,290 in which a bayonet interconnection is provided between the reamer and the driver.

Typically, surgeons use specialized drivers for each of the reamers. The drivers connect to a source of power and have appropriate handles for guiding the operation of the reamer by a surgeon. If a surgeon has one of the adaptors, it is difficult to utilize the other type of reamer since it requires a specialized driver for that reamer. It has been proposed in U.S. Pat. No. 7,115,119 to provide a dual adapter that accommodates both the Othy and the Precimed reamers. However, this style of dual reamer requires a bayonet interconnection in which the assemblies are inserted axially and then a rotational movement, in accordance with a bayonet connection, is provided to lock the elements in place. This type of action slows the process of utilizing a new reamer because of the additional movement, But, more than that, the release of the device, after it has been in the surgical environment, is more difficult because it requires holding the reamer to reverse the rotational movement and then axial movement to finally free the reamer.

What is needed in the art, therefore, is a tool driver for surgical reamers that enables rapid and immediate connection and disconnection of the reamers.

SUMMARY OF THE INVENTION

In one form, the invention is a tool driver for multiple styles of surgical reamers. The driver includes a central shaft rotatable about a longitudinal axis and having a proximal driven end and a distal end. A reamer receiver is carried by the distal end of the shaft and the receiver has axially facing sets of recesses for receiving at least two different styles of surgical reamers. A gripping device is provided for releasably holding the surgical reamer assemblies in place, the releasable holding device permitting axial removal of the different styles of surgical reamers.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one embodiment of the invention and such exemplifications are not to be construed as limiting the scope of the invention in any manner.

DETAILED DESCRIPTION OF THE INVENTION

Figure 1:
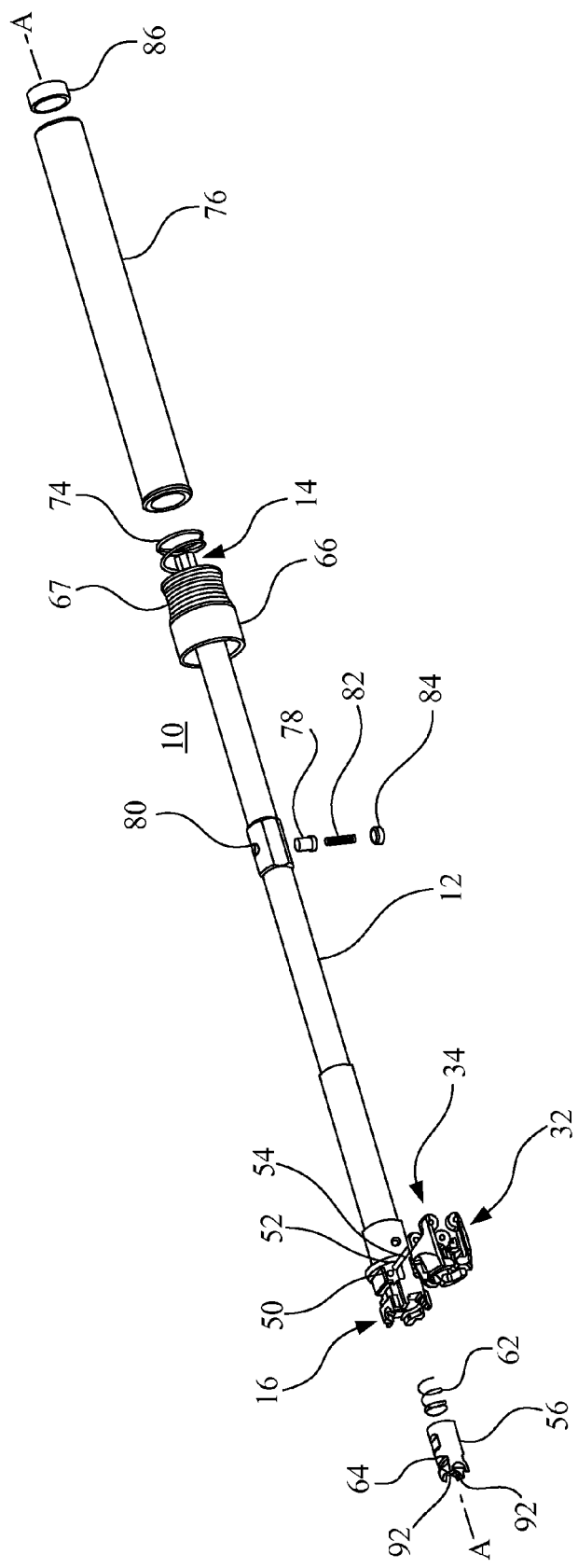
FIG. 1 is an exploded perspective view of a tool driver in accordance with the present invention.

FIG. 1 shows an exploded view of a reamer driver 10 in accordance with the present invention. Reamer driver 10 has a central shaft 12 rotatable about a longitudinal axis A at an RPM that is appropriate for removal of material during a surgical procedure. Shaft 12 has a proximal end 14 with an interface having an appropriate to receive a power element to produce the correct torque and RPM to perform the surgical removal of material.

Figure 3:
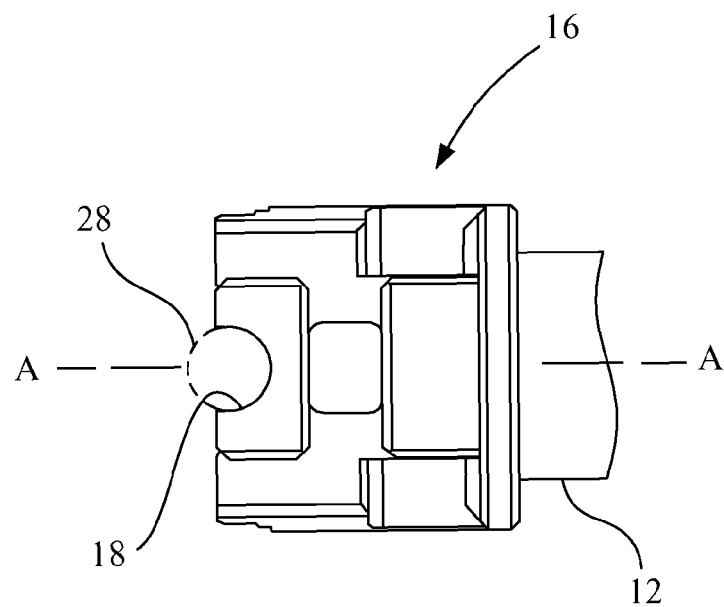
FIG. 3 is an expanded detailed view of a portion of the tool driver in FIGS. 1 and 2 taken in the same plane as FIG. 2.
Figure 4:
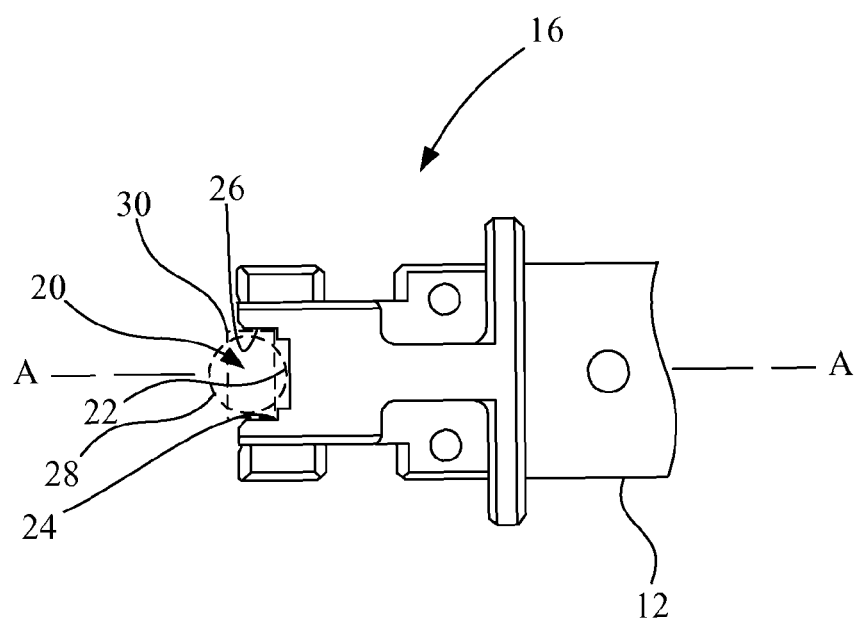
FIG. 4 is an enlarged detailed view of a portion of the tool driver shown in FIG. 2 taken on a plane at 90 degrees to the plane of FIG. 2.

Central shaft 12 has a distal end 16 for receiving one of a plurality of different styles of surgical reamers. As shown particularly in FIGS. 3 and 4, distal end 16 has a plurality of recesses integrally formed with the end of shaft 12. It should be apparent, however, to those skilled in the art that the recesses may be formed in a separate element that is affixed to the end of shaft 12. A pair of recesses 18 are semicircular in cross section as shown in FIG. 3. Recesses 18 are formed in portions of the distal end 16 offset from the central axis A and permit movement directly in an axial direction as shown in FIG. 3. FIG. 4 shows a pair of recesses 20 including a base 22 and a shoulder 24 connecting to sidewalls 26. Recesses 20 are positioned at 90 degrees relative to recesses 18.

As stated previously there are two major styles of reamers in the surgical field, one of which is a crossbar and the other of which is a cross bridge. The crossbar interface is illustrated by dashed lines 28, shown in FIG. 3 and FIG. 4. It is to be noted that the base of semicircular recess 18 and recess base 22 are in the same plane so that the interface for the crossbar reamer 28 is positioned in a common plane to stabilize it. The other surgical reamer is an Othy cross bridge reamer having a circular center and two radially extending bars illustrated by dashed line 30. The crossbridge reamer 30 rests on the shoulder 24. The cross bridge reamer is also moveable into and out of the recesses 20 in an axial direction as illustrated in FIG. 4.

Figure 2:
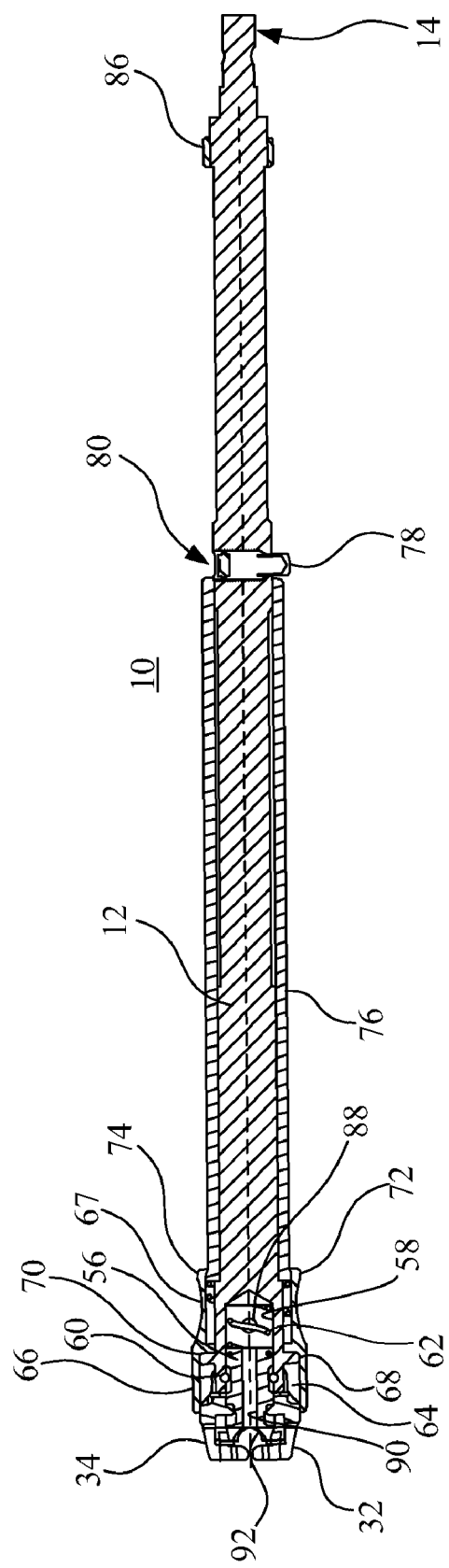
FIG. 2 is a longitudinal section view of the tool driver shown in FIG. 1.
Figure 2A:
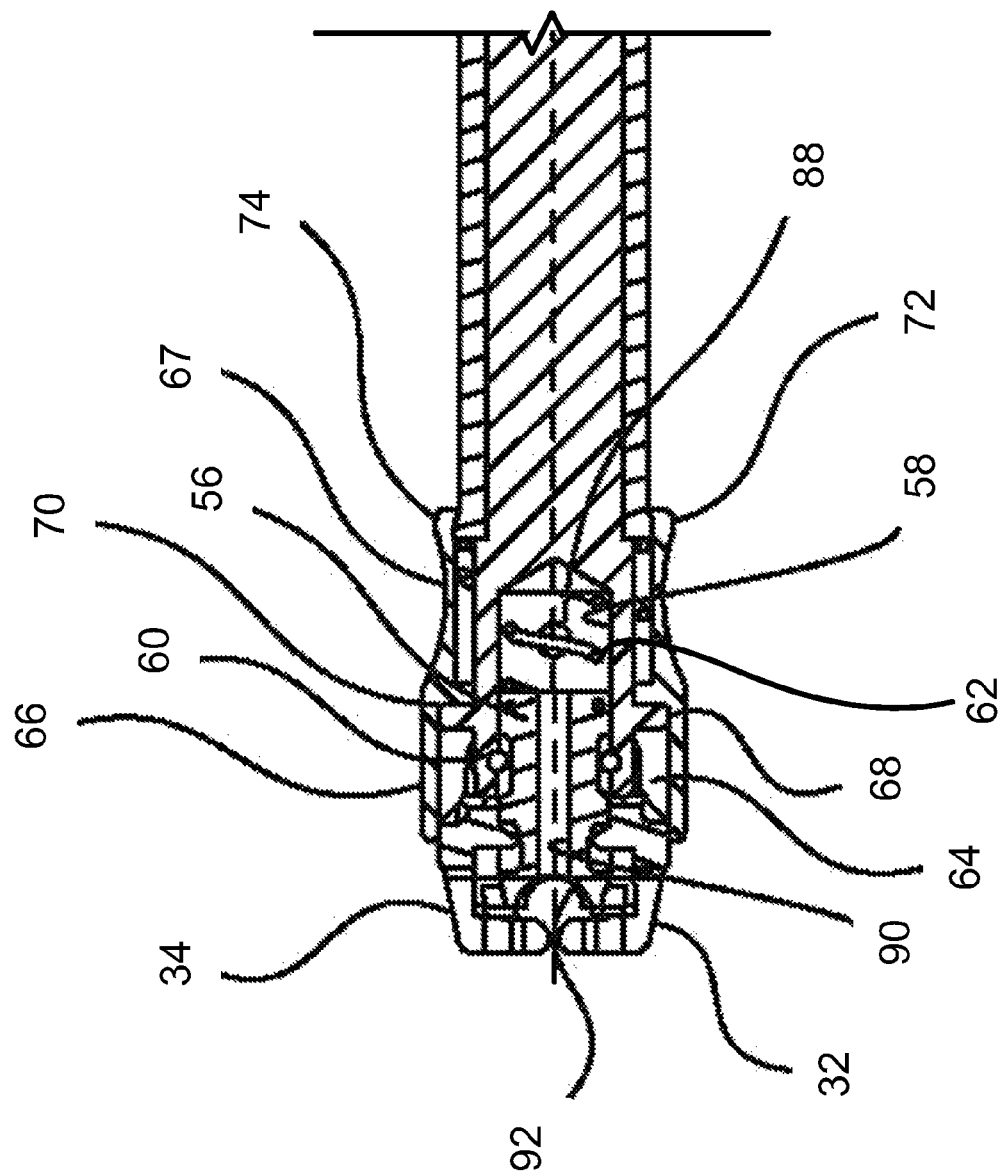
FIG. 2a is an expanded view of FIG. 2.
Figure 5:
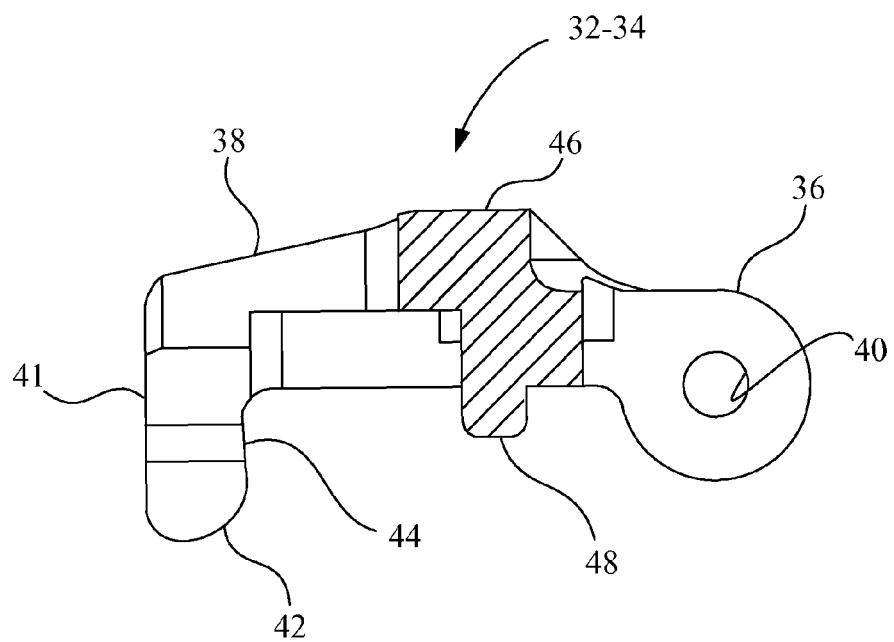
FIG. 5 is a side view of an element of the tool driver shown in FIGS. 1-4.
Figure 6:
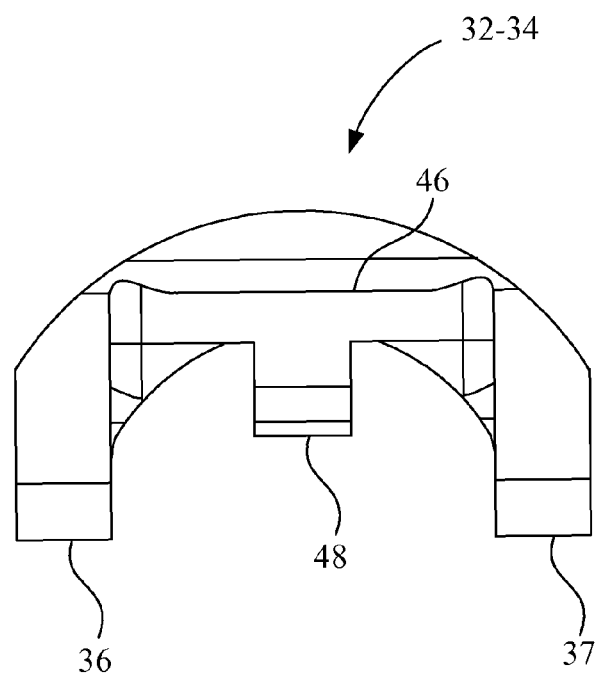
FIG. 6 is a top view of the element shown in FIG. 5.

The different styles of reamers 28 and 30 are retained within the recesses 18 and 24 by grips 32 and 34 shown in FIGS. 2 and 3 and in detail in FIGS. 5 and 6. The grips 32 and 34 are identical so that reference characters used in FIGS. 5 and 6 are applicable for both grips. Grips 32-34 comprise base elements 36 and 37 having central aligned bores 40 to provide a pivotal mounting on central shaft 12. Bases 36 extend to integral gripping elements 38 having an L-shaped extension 41 so that the grips 32-34 form an L-shape with a pivotal mounting at one end of the L. The extension 41 has a gripping surface 42 with a contour that provides a negative angle with respect to the center of bore 40 so as to accommodate varying thicknesses of reamers. Generally speaking the surface 44 has approximately a 4 degree angle with respect to a plane at right angles to a line extending through bore 40. An intermediate section 46 has a camming surface 48 projecting downward as shown in FIGS. 5 and 6 to interact with elements of the reamer driver 10 disclosed below.

The grips 32 and 34 are pivotally connected to shaft 12 at surfaces 50 with a through hole 52 by a pin 54 extending through bore 40 and through hole 52. Thus, the grips 32 and 34 are mounted so as to grip or release the respective reamers 28 and 30 in an axial direction. FIG. 2 shows the grips 32 and 34 in the retention position.

Grips 32 and 34 are biased to the open position permitting removal of the reamers 28 or 30. As shown in FIGS. 1 and 2, this is done by a central plunger 56 received in an axial bore 58 of central shaft 12. Plunger 56 is retained within the bore 58 by a removable ring 60 and is biases towards the left by a spring 62 retained within bore 58. Plunger 56 has a shoulder 64 that acts as a camming surface for the corresponding camming surface 48 on grips 32-34 so as to displace them in a radially outward direction upon axial movement of plunger 56 towards the distal end of shaft 12. Thus, in the absence of any restraining element, the grips 32 and 34 are urged to their open position.

The grips 32-34 are urged to the closed position illustrated in FIG. 2 by a sleeve 66 telescoped over shaft 12. Sleeve 66 has an inwardly facing shoulder 68 which abuts a corresponding outwardly facing shoulder 70 on shaft 12 to limit the left most position of sleeve 66. Sleeve 66 has a suitable serrated gripping surface 67 to enable manual manipulation. Sleeve 66 is urged to the leftmost position by a spring 74 retained over shaft 12 and abutting a protective sleeve 76, also telescoped over shaft 12.

Protective sleeve 76 is retained on shaft 12 by a pin 78 received in a cross bore 80 of shaft 12 and yieldably urged to the position shown in FIG. 2 by a spring 82. An appropriate cap 84 retains spring 82 within the bore 80. A retention sleeve 86 is appropriately affixed to the proximal end 14 of shaft 12 so as to limit the rightmost movement of protective sleeve 76.

In order to facilitate cleaning of the reamer driver, radial passages 88 are provided from recess 58 to the exterior and a central passage 90 is provided in plunger 56. In addition, plunger 56 has cross semicircular recesses 92 at 90 degrees to one another to abut the crossbars of reamer style 28 so as to further stabilize it.

The reamer driver 10 is operated by pulling sleeve 66 to the right as viewed in FIG. 2 so as to free the grips 32 and 34 and permit the spring 62 to displace the plunger 56 axially so that shoulder 64 urges the camming surface 48 radially outward. The arc of movement is sufficient to permit the surfaces 42 of grips 32-34 to provide axial clearance permitting removal or installation of the reamer driver styles 28 and 30 in an axial direction only. While the sleeve 66 is retracted, either reamer driver style 28 or 30 is axially inserted into the appropriate recesses and the plunger 56 is displaced to the right as shown in FIG. 2. In the case of reamer style 28, the semicircular recesses 92 embrace the crossbars so as to stabilize the reamer. In the case of reamer style 30, the end of plunger 56 abuts the undersurface of the crossbridge reamer 30. The displacement of the plunger 56 to the right permits the grips 32 and 34 to be acted on by sleeve 66 as urged by spring 74. This action holds the drivers in place for a surgical procedure. When the surgical procedure is completed, the sleeve 66 is simply displaced axially to the right as shown in FIG. 2 and the plunger 56 automatically urges either driver style from the driver assembly, thus eliminating multiple movements during a surgical procedure.

In addition to providing a simplified axial movement for connection and removal, the displacement of pin 78 permits the protective sleeve 76 to be moved to the right against retention sleeve 86, thus allowing total expansion of the grips 32 and 34 for cleaning. The radial passages provided in plunger 66 and in the sidewall of recess 58 also facilitate the cleaning of the assembly.

The angle provided on surface 44 of grip 32-34 enables the retention of a range of thicknesses for the reamers 28 and 30.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tool driver for driving multiple styles of surgical reamers, said driver comprising:
   a central shaft rotatable about a longitudinal axis and having a proximal end and a distal end; said central shaft comprises an axially facing pair of diametrical recesses perpendicular to one another at said distal end for receiving at least two different styles of surgical reamers only in an axial direction, said pair of diametrical recesses includes a first portion having a semicircular recess for receiving a cross-bar style reamer and a second portion having a recess base and shoulders connecting to sidewalls of said recesses for receiving a cross-bridge style reamer, wherein said semicircular recess and said recess base are in the same plane;
   a gripping device for releasably holding said surgical reamer assemblies in place in said pair of diametrical recesses, said gripping device comprising at least one pair of L-shape elements and a sleeve,
   said at least one pair of L-shape elements are pivotally mounted to adjacent opposite sides of said central shaft at said distal end and being pivotal between a retention position and an open position permitting direct axial removal and installation of the different styles of surgical reamers, each of said L-shaped gripping elements comprises a first section at a first end for pivotal mounting to said central shaft, a second opposing free end having an extension extending radially inward for capturing and holding different style reamers in said recesses, and an intermediate camming surface facing said longitudinal axis of said central shaft; and said sleeve is telescoped over said central shaft, wherein said sleeve being yieldably urged to hold said L-shape gripping elements in place;

said central shaft further comprises an axial bore at said distal end and a plunger being axially received in said axial bore; said plunger interacting with said gripping device to urge said at least one pair of opposing L-shaped gripping elements from said retention position to said open position upon axial movement of said plunger in said bore, said plunger comprises a pair of cross semicircular recesses extending diametrically and perpendicular to one another at a distal end of said plunger and opens in an axial direction for abutting and stabilizing at least one reamer therein; wherein said plunger further comprises a shoulder that acts as a camming surface for interacting with said camming surface of said L-shape gripping elements and urges said at least one pair of L-shaped gripping elements from said retention position to said open position upon axial movement of said plunger in said bore;

a spring being retained within said axial bore for yieldably urging said plunger in an axial direction relative to said central shaft and urging said L-shape gripping elements to said open position thereby releasing said at least two different styles of reamers, such that in said open position said two different styles of reamers are automatically released and ejected from said central shaft in an axial direction.

2. The tool driver as claimed in claim 1 wherein said first section of said L-shaped gripping elements has a central aligned hole for pivotally mounted to said central shaft and said extension at said second free end has a gripping surface with a contour that provides a negative angle with respect to said central aligned hole to accommodate reamers of varying thickness.

3. The tool driver as claimed in claim 1 wherein said central shaft has a radial passage extending from said axial bore of said central shaft at said distal end to the exterior for enhancing cleaning of the tool driver.

4. The tool driver as claimed in claim 1 wherein said sleeve is removably telescoped over the exterior of said central shaft.

5. The tool driver as claimed in claim 4 further comprising a radially extending pin yieldably urged radially outward on said shaft remote from said distal end for providing an abutment for said telescoped sleeve, said pin being urgeable inward to release said telescoped sleeve to provide access for cleaning.

6. The tool driver as claimed in claim 5 further comprising a stop ring secured to said shaft adjacent its proximal end for permanently holding said sleeve on said shaft.

* * * * *